United States Patent [19]

Gattuso

[11] 4,041,043

[45] Aug. 9, 1977

[54] PARTICULARLY SUBSTITUTED THIAZOLESULFENAMIDES

[75] Inventor: Marion J. Gattuso, Hoffman Estates, Ill.

[73] Assignee: UOP Inc., Des Plaines, Ill.

[21] Appl. No.: 637,994

[22] Filed: Dec. 5, 1975

Related U.S. Application Data

[63] Continuation-in-part of Ser. No. 399,213, Sept. 20, 1973, abandoned, which is a continuation-in-part of Ser. No. 139,145, April 30, 1971, abandoned, which is a continuation-in-part of Ser. No. 100,508, Dec. 21, 1970, abandoned.

[51] Int. Cl.² ............................................. C07D 277/80
[52] U.S. Cl. ............................. 260/306.6 A; 260/800
[58] Field of Search ................................. 260/306.6 A

[56] References Cited

U.S. PATENT DOCUMENTS

| 2,370,253 | 2/1945 | Messer | 260/306.6 A |
| 2,992,228 | 7/1961 | D'Amico | 260/306.6 A |

OTHER PUBLICATIONS

Gattuso et al., Chem. Abs. 77, 114393a (1972).
Gur'yanova et al., Chem. Abs. 57, 85555; (1961).
Fel'dshtein et al. Chem. Abs. 56, 1576; (1961).

*Primary Examiner*—Donald G. Daus
*Assistant Examiner*—Mark L. Berch
*Attorney, Agent, or Firm*—James R. Hoatson, Jr.; Raymond H. Nelson; William H. Page II

[57] ABSTRACT

Novel compounds comprising N-phenyl-N-R-benzothiazole-2-sulfenamides in which R is an akyl radical or cycloalkyl radical are useful as rubber additives.

2 Claims, No Drawings

PARTICULARLY SUBSTITUTED THIAZOLESULFENAMIDES

CROSS-REFERENCE TO RELATED APPLICATIONS

This application is a continuation-in-part of my copending application Ser. No. 399,213 now abondoned filed Sept. 20, 1973, which is a continuation-in-part of my copending application Ser. No. 139,145 filed Apr. 30, 1971 and now abandoned, which is a continuation-in-part of my copending application Ser. No. 100,508 filed Dec. 21, 1970 and now abandoned.

BACKGROUND OF THE INVENTION

The prior art has shown certain compounds comprising substituted thiazolesulfenamides or thiazoles. One such reference discloses the compounds comprising the oxidative condensation products of organic mercaptans and amines. However, the amines which are used in the process of the prior art reference are stronger than ammonia, the amino nitrogen atoms possessing a dissociation constant greater than $1.8 \times 10^{-5}$. In contradistinction to this, the amines which are utilized as one of the starting materials to prepare the compounds of the present process are less basic than ammonia. In addition, another prior reference discloses sulfenamides which are prepared from primary amines and will posses only one substituent of the nitrogen other than hydrogen. The compound of this reference also differs from the compounds of the present invention which comprise disubstituted benzothiazole-2-sulfenamides in which one of the substituents is a phenyl radical. Other references which are found in the prior art include derivatives of N-betacyanoethylbenzothiazolesulfenamides in which each of the compounds disclosed in the reference requires the presence of a cyanoethyl substituent of the nitrogen atom. Another reference has been found in the prior art which discloses a diphenyl-substituted compound for use as a vulcanization accelerator. However, it is stated in the reference that the introduction of two phenyl radicals in the group of a sulfenamide compound results in a total loss of vulcanization activity while replacement of one phenyl radical with a hydrogen atom (in other words a mono-substituted sulfenamide) creates a compound which is a effective vulcanization accelerator. Other references have also disclosed substituted benzothiazolesulfenamides containing halogen atoms which are used as accelerators in the vulcanization of rubber or mono-substituted arylene thiazylsulfenamides which are also used as accelerators in the vulcanization of rubber. As will be hereinafter shown, this is in contradistinction to the findings of the present invention which discloses an effective vulcanization accelerator comprising a disubstituted sulfenamide, one of which is a phenyl radical and the other of which is an alkyl or cyloalkyl radical. Furthermore, there is no teaching in the art of the ability of the compounds of the present invention to decrease the scorch time in admixtures with an antiozonant and rubber.

This invention relates to novel compounds comprising N-phenyl-N-R-thiazole-2-sulfenamides in which the R is an alkyl or cyloalkyl radical of the type hereinafter set forth in great detail.

The N,N-disubstituted-thiazole-2-sulfenamides which comprise the novel compounds of the present invention and in which one substituent on the nitrogen atom is a phenyl and the other substituent is an alkyl or cycloakyl radical, will have varied utility. In particular, the compounds may be useful as additives to rubber. As a particular advantage in such use, the N,N-disubstituted-benzothiazole-2-sulfenamide serves to offset the decrease in scorch time which occurs when a secondary diamine antiozonant is incorporated in the rubber formulation. The phenyl and R groups in the above formula will be selected with reference to the particular rubber properties desired inasmuch as they appear to react somewhat differently in different rubber formulations.

In one aspect an embodiment of this invention resides in N-phenyl-N-R-benzothiazole-2-sulfenamide in which R is an alkyl radical of from 3 to about 20 carbons atoms or a cycloalkyl radical of from 4 to 6 carbons atoms.

A specific embodiment of this invention is found in a compound useful as a rubber additive comprising N-phenyl-N-butylbenzothiazole-2-sulfenamide.

Other objects and embodiments will be found in the following further detailed description of the present invention.

As hereinbefore set forth the present invention is concerned with novel compounds comprising N,N-disubstituted-benzothiazole-2-sulfenamides in which one of the substituents on the nitrogen atom is a phenyl radical while the other substituent is an alkyl radical containing from 3 to 20 carbon atoms and preferably in a range of from 3 to 12 carbon atoms, or a cycloalkyl radical containing from 4 to 12 carbon atoms and preferably from 4 to 6 carbon atoms. These compounds will posses the generic formula: N-phenyl-N-R-benzothiazole-2-sulfenamide, in which R possesses the above description. Illustrative novel compounds of the present invention will include N-phenyl-N-propylbenzothiazole-2-sulfenamide, N-phenyl-N-butylbenzothiazole-2-sulfenamide, N-phenyl-N-pentylbenzothiazole-2-sulfenamide, N-phenyl-N-hexylbenzothiazole-2-sulfenamide, N-phenyl-N-heptylbenzothiazole-2-sulfenamide, N-phenyl-N-octylbenzothiazole-2-sulfenamide, N-phenyl-N-nonylbenzothiazole-2-sulfenamide, N-phenyl-N-decylbenzothiazole-2-sulfenamide, N-phenyl-N-undecylbenzothiazole-2-sulfenamide, N-phenyl-N-dodecylbenzothiazole-2-sulfenamide, N-phenyl-N-tridecylbenzothiazole-2sulfenamide, N-phenyl-N-tetradecylbenzothiazole-2-sulfenamide, N-phenyl-N-pentadecylbenzothiazole-2-sulfenamide, N-phenyl-N-hexadecylbenzothiazole-2sulfenamide, N-phenyl-N-heptadecylbenzothiazole-2sulfenamide, N-phenyl-N-octadecylbenzothiazole-2-sulfenamide N-phenyl-N-nonadecylbenzothiazole-2-sulfenamide, N-phenyl-N-eicosylbenzothiazole-2-sulfenamide, N-phenyl-N-cyclobutylbenzothiazole-2-sulfenamide, N-phenyl-N-cylclopentylbenzothiazole-2-sulfenamide, N-phenyl-N-cyclohexylbenzothiazole-2-sulfenamide, N-phenyl-N-cycloheptylbenzothiazole-2-sulfenamide, N-phenyl-N-cyclooctylbenzothiazole-2-sulfenamide, N-phenyl-N-cyclononylbenzothiazole-2-sulfenamide, N-phenyl-N-cyclodecylbenzothiazole-2-sulfenamide, N-phenyl-N-cycloundecylbenzothiazole-2-sulfenamide and N-phenyl-N-cyclododecylbenzothiazole-2-sulfenamide, etc. It is understood that the alky group may be of straight or branched chain and also of primary, secondary or tertiary configuration.

The N,N-disubstituted-thiazole-2-sulfenamide of the present invention may be prepared in any suitable manner. In a particularly preferred method, a thiazole-2sulfenamide is reacted with an arylamine acid salt such as an aniline acid salt. The thiazole-2-sulfenamide may be obtained from any suitable source or prepared in accordance with any of the various methods previous disclosed in the art. In a preferred embodiment, benzothiazole-2-sulfenamide is utilized as one of the reactants and, in another embodiment, the amide moiety may contain or two alkyl substituents, preferably containing from 3 to about 6 and more particularly from 3 to 4 carbon atoms. For example, N-tert-butylbenzothiazole-2sulfenamide is available in the open market and, as will be shown in the appended examples, has been used for the preparation of N-phenyl-N-R-substituted derivatives.

In this method of preparation, the thiazole-2-sulfenamide is reacted with an N-substituted aniline acid salt. Any suitable acid salt of aniline may be used. Particularly preferred salts will include the hydrohalide salts such as hydrochloride salts, hydrobromide salts, hydroiodide salts, etc., with the hydrochloride salts being especially preferred. Other acid salts include the sulfate, phosphate, nitrate, as well as organic acid salts and particularly the formate, acetate, propionate, butyrate, oxalate, malonate, benzoate salts, etc. When the R in the generic formula of the compound is alkyl, the acid salt of $N-C_3-C_{20}$-alkylaniline is used as a reactant and similarly when R in the formula is cycloalkyl, the acid salt of $N-C_4-C_{12}$-cycloalkylaniline is used as a reactant.

The aniline acid salt may be obtained from any suitable source or may be prepared in any suitable manner. A number of these acid salts are available commercially and accordingly are conveniently used in the present invention. The hydrochloride salt may be prepared, for example, by dissolving the aniline in a suitable solvent, such as diethyl ether, and adding concentration hydrochloric acid thereto, with intimate stirring until no further precipitation occurs. The precipitate is then filtered from the solution and washed with ether, followed by drying either in air or otherwise.

The thiazole-2-sulfenamide and the N-substituted aniline acid salt are reacted in any suitable manner. As a particular advantage to this method of preparation, the reaction occurs readily and, accordingly, required minimum time, which may range from 5 minutes to 1 hour and more particularly from 10 minutes to 30 minutes. The reaction is readily effected at room temperature although, when desired, a higher temperature may be used which preferably is below about 100° C. The reaction is effected by forming a solution of one or both the reactants, which may be mildly heated to facilitate solubility. Any suitable solvent may be used and conveniently comprises an alcohol such as methanol, ethanol, propanol, butanol, etc., a ketone as acetone, methyl ethyl ketone, diethyl ketone, etc., dioxane, hydrocarbons such as benzene, toluene, pentane, hexane, etc., an amide such as dimethylformamide, etc., or mixtures of these with each other or with water. The solvent employed preferably is one in which both reactants are mutually soluble, although partial solubility of the reactants in the solvent may be satisfactory as with water, ether, etc., but may require longer time in mixing to insure complete reaction. Because the solvent is subsequently removed by evaporation, it is preferred to use a lower boiling solvent for ready evaporation from the product.

In instances where the thiazolesulfenamide for use as a reactant contains impurities, such as disulfides, it may be desirable to filter the solution of sulfenamide prior to commingling with the aniline acid salt. Similarly, when the aniline acid salt contains impurities which can be removed by filtering, the solution of the aniline acid salt preferably is filtered prior to use.

The thiazolesulfenamide and aniline acid salt are reacted in equimolar proportions. However, an excess of the sulfenamide or aniline acid salt may be employed, which excess generally will not exceed about 4:1 molar proportions and thus the reactants may be used in a mole proportion of from 1:1 to 4:1.

The thiazolesulfenamide and aniline acid salt are reacted in any suitable manner. As hereinbefore set forth, this requires merely intimate mixing of the reactants in contact with the solvent. In one method, the solid product may be removed by filtering and in another method, particularly when the product is soluble in the solvent, the solvent is evaporated in any suitable manner, preferably under vacuum, and the product recovered as a solid precipitate. The ammonium chloride or other ammonium salt formed in the reaction is removed in any suitable manner and preferably by washing with water. To facilitate removal of the ammonium salt, the solid may first be dissolved in ether and then water washed. The resultant mixture may be dried, in any suitable manner, such as by being contacted with magnesium sulfate, etc., and then the ether removed be evaporation. The product may be further purified as desired by crystallization from ether, benzene or other suitable agent.

While the above method of preparation is preferred, it is understood that any other suitable method may be used. One other method is reacting the thiazolesulfenamide with the N-substituted aniline at 30° to about 100° C. in a solvent and continuously removing the ammonia or amine evolved in the reaction. In still another method, the reaction is effected by the oxidative condensation in alcohol solvent and alkali metal hypochlorite at a temperature below 0° C. Any other suitable method of preparation may be used.

As hereinbefore set forth, a preferred use is to offset the decrease in scorch time encountered when using an antiozonant. In one embodiment, the antiozonant is of the phenylenediamine type and includes, for example, N,N'-di-sec-alkyl-p-phenylenediamine in which the alky contains from 3 to 12 carbon atoms, N-phenyl-N'-sec-alkyl-p-phenylenediamine, in which the alkyl contains 3 to 12 carbon atoms, N,N'-dicyclohexyl-p-phenylenediamine, N-phenyl-N'-cyclohexyl-p-phenylenechlorine etc. In another embodiment, the antiozonant is of the aminophenol type and includes $N-C_3C_{20}$-alkyl-p-aminophenol, N-cycloalkyl-p-aminophenol in which the cycloalkyl ring contains from 4 to 12 carbon atoms, etc. The antiozonant may be used in a concentration of from 1 to about 5 parts by weight per 100 parts of rubber hydrocarbon in the formulation.

The N,N-disubstituted-benzothiazole-2-sulfenamide of the present invention is used in the rubber formulation in a concentration of from 0.5 to about 3 and preferably from 1 to 2 parts of the sulfenamide per 100 parts of the rubber hydrocarbon in the formulation. The sulfenamide of the present invention is incorporated in the rubber formulation in any suitable manner and conveniently is incorporated during milling of the various ingredients including, in addition to the sulfenamide of the present invention, carbon, zinc oxide, sulfur, stearic acid, antioxidant, antiozonant, etc., all of these being used in conventional concentrations. As another means of controlling the curing of the rubber stock, additional compounds may also be included in rubber formulation as, for example, thiuram disulfides, N-alkyl-sulfenamides, cyclohexlamine, N-cyclohexylthiopthalimide, mercaptobenzothiazole or other sulfenamides, etc., and/or an excess of sulfur may be used. These additional compounds will be selected for use in conjunction with the N,N-disubstituted-benzothiazole-2-sulfenamide of the present invention to produce a formulation having the desired scorch time and the desired vulcanization to prepare a rubber product of desired physical properties. The vulcanization is effected in conventional manner.

The following examples are introduced to illustrate further the novelty of the compounds of the present invention and the utility of the same, however, but not with the intention of unduly limiting the same.

EXAMPLE I

This example describes the preparation of N-ethyl-N-phenylbenzothiazole-2-sulfenamide which was prepared by dissolving 23.8 grams (0.1 mole) of N-tert-butylbenzothiazole-2-sulfenamide in 200 ml of methanol and separately dissolving 15.7 grams (0.1 mole) of N-ethylaniline hydrochloride in 100 ml of methanol. The two solutions were filtered into a 1000 ml flask and stirred. The crude product was 25.7 grams which is 93% yield. Purification by elution chromatography on basic alumina gave a slightly yellow viscous oil. Elemental analysis showed 63.10% carbon, 4.92% hydrogen, 22.9% sulfur and 9.28% nitrogen which correspond to the calculated values of 62.90% carbon, 4.93% hydrogen, 22.39% sulfur and 9.78% nitrogen.

EXAMPLE II

It is believed that the preparation of Example I probably contains some impurity which precluded the precipitation of solid product. Another preparation of the same compound was made by reacting at room temperature 31.4 grams (0.2 mole) of N-ethylaniline hydrochloride and 47.69 grams (0.2 mole) of N-tert-butylbenzothiazole-2-sulfenamide in 100 ml of methanol for ca. 1 hour. Then 100 ml of water and about 100 ml of chloroform were added to the above solution, with stirring. The chloroform fraction was dried and the solvent removed to leave 52.5 grams (92% yield of a dark green oily liquid. The liquid was taken up in a small amount of hot methanol and allowed to stand for ca.48 hours. After this time, a large amount of white needles (ca. 25 grams) had crystallized. These were recrystallized from a methanol/benzene solution to yield N-ethyl-N-phenylbenzothiazole-2-sulfenamide as clear needles having a melting point of 51°-52° C. The decanted mother liquid (dark green in color) was allowed to stand, and an additional amount of crystals was obtained. Elemental analysis of the white crystals showed 63.04% carbon, 4.95% hydrogen, 24.5% sulfur and 10.25% nitrogen, which correspond to the calculated values of 62.9% carbon, 4.93% hydrogen, 9.78% nitrogen and 22.39% sulfur.

EXAMPLE III

In this example 36.2 grams (0.2 mole) of benzothiazole-2-sulfenamide are dissolved in 200 ml of methanol while 36.9 grams (0.2 mole) of N-butylaniline hydrochloride are separately dissolved in 100 ml of methanol. The two solutions are filtered into a 1000 ml flask and stirred at room temperature for about 1 hour. At the end of this time, 100 ml of water and about 100 ml of chloroform are added with stirring. The chloroform fraction is dried and the solvent is removed following which the liquid which remains is taken up with hot methanol and allowed to stand for a period of about 48 hours. The white crystals which formed at the end of this time are recrystallized from a methanol-benzene solution to yield the desired product comprising N-phenyl-N-butylbenzothiazole-2-sulfenamide.

EXAMPLE IV

In a manner similar to that set forth in the above examples 19.7 grams (0.1 mole) of N-cyclopentylaniline hydrochloride is dissolved in methanol while 18.1 grams (0.1 mole) of benzothiazole-2-sulfenamide are separately dissolved in an additional amount of methanol. The two solutions are combined and allowed to react for a period of about 1 hour at room temperature. At the end of this time, the solution is filtered and treated in a manner similar to that hereinbefore set forth whereby the desired compound comprising N-phenyl-N-cyclopentylbenzothiazole-2-sulfenamide is separated and recovered.

EXAMPLE V

To 100 ml of methanol is added 21.0 grams (0.1 mole) of N-cyclohexylaniline hydrochloride while 18.1 grams (0.1 mole) of benzothiazole-2-sulfenamide are added to a separate 100 ml portion of methanol. The two solutions are admixed and stirred at room temperature for a period of 1 hour. At the end of this time, an additional amount of water and chloroform is added to the solution accompanied by vigorous stirring. The chloroform fraction is dried and the solvent is removed following which the liquid is again taken up hot methanol and allowed to stand for a period of about 48 hours. The crystalline material which has crystallized at the end of this period is recrystallized from methanol-benzene solution to yield the desired product comprising N-phenyl-N-cyclohexylbenzothiazole-2-sulfenamide.

EXAMPLE VI

In a manner similar to that hereinbefore described 29.7 grams (1.0 mole) of N-dodecylaniline hydrochloride are dissolved in methanol and 23.4 grams (0.1 mole) of N-tert-butylbenzothiazole-2-sulfenamide are dissolved in a separate methanol solution. The two solutions are combined within intimate stirring for a period of 1 hour. Following completion of the reaction, the product is worked up in substantially the same manner as hereinbefore described whereby the desired product comprising N-phenyl-N-dodecylbenzothiazole-2-sulfenamide is recovered.

EXAMPLE VII

As hereinbefore set forth the N,N-disubstituted-benzothiazole-2-sulfenamides in which one of the substituents is a phenyl radical and the other substituent is an alkyl or cycloalkyl radical will serve to offset the decrease in scorch time encountered when a phenylenediamine antiozonant is incorporated in the rubber formulation. It is desirable, and often necessary, to incorporate an antiozonant into the rubber formulation in order to protect the rubber from deterioration due to ozone attack.

This example reports the Mooney scorch properties of an SBR (styrene-butadiene-rubber) formulation in which 1.25 phr (parts per 100 parts of rubber hydrocarbon) of N-phenyl-N-ethylbenzothiazole-2-sulfenamide antiozonant were incorporated in a rubber formulation. The remaining ingredients of the rubber formulation were 100 parts by weight of SBR 1502, 40 parts by weight of furnace black, 3 parts by weight of zinc oxide, 2 parts by weight of stearic acid and 2 parts by weight of sulfur. This ingredients were incorporated by conventional milling procedure and the formulation was cured for 40 minutes at 140° C.

The scorch values were determined with a large rotor Mooney viscometer at 250° C. (ASTM D-1077-55T). The values represent the number of minutes for a rubber containing a curing agent to increase in viscosity by 5 and then by 20 points. This method simulates conditions encountered during milling and subsequent vulcanization. A high scorch value indicates a high resistance to scorching. The Mooney scorch values of the formulation containing both the N-phenyl-N-ethylbenzothiazole-2-sulfenamide and the phenylenediamine antiozonant were 34.0 for the 5 point rise and 44.6 for the 20 point rise.

For comparative purposes, a similar formulation which contained N-tert-butylbenzothiazole-2-sulfenamide instead of the sulfenamide of the present invention gave a 5 point rise of 19.5 and a 20 point rise of 21.2. It will be noted that the N-tert-butylbenzothiazole-2 sulfenamide is a commercial compound used in rubber formulations. The considerable retarding of scorch when using the N-phenyl-N-ethylbenzothiazole-2-sulfenamide of the present invention is evident from a comparison of the above results.

EXAMPLE VIII

This example illustrates the use of N-ethyl-N-phenylbenzothiazole-2-sulfenamide, prepared as described in Example II, as a scorch retarder in nitrile rubber. The nitrile rubber is compounded in conventional manner to include 3.5 phr of N-phenyl-N'-sec-octyl-p-phenylenediamine and 1.25 phr of N-ethyl-N-phenylbenzothiazole-2-sulfenamide. Here again the rubber will be protected against ozone cracking and also has a longer scorch value.

EXAMPLE IX

Natural rubber is compounded in a conventional manner to contain 3 phr of N-phenyl-N'-(1,3-dimethylbutyl)-p-phenylenediamine antiozonant and 1.5 phr of N-phenyl-N-butylbenzothiazole-2-sulfenamide, prepared as described in Example III. The ruber is protected agianst ozone cracking and also possesses a high scorch value.

EXAMPLE X

In like manner when an SBR (styrene-butadiene-rubber) formulation which contains 2 phr of N,N'-di-sec-octyl-p-phenylenediamine antiozonant and 1.25 phr of N-phenyl-N-cyclopentylbenzothiazole-2-sulfenamide is subjected to a test similar in nature to that set forth in Example VIII, it will be found that the rubber is protected against ozone cracking and will also possess a high Mooney scorch value.

EXAMPLE XI

In this example a nitrile rubber is compounded in a conventional manner to include 3.5 phr of N-phenyl-N'-sec-octyl-p-phenylenediamine antiozonant and 1.25 phr of N-phenyl-N-cyclohexylbenzothiazole-2-sulfenamide as a scorch retardant. After subjecting the formulation to a test for scorch values, it will be found that the rubber will be protected against ozone cracking and will also posses a longer scorch value.

A similar test with nitrile rubber using N-phenyl-N-dodecylbenzothiazole-2-sulfenamide along with N-phenyl-N'-sec-octyl-p-phenylenediamine will provide similar results, that is, the rubber will be protected against ozone cracking and will possess a longer value than rubber which does not contain the sulfenamide.

I claim as my invention:
1. An N-phenyl-N-alkyl-benzothiazole-2-sulfenamide in which the sulfenamide is N-phenyl-N-sec-octylbenzothiazole-2-sulfenamide.
2. An N-phenyl-N-alkyl-benzothiazole-2-sulfenamide in which the sulfenamide is N-phenyl-N-dodecylbenzothiazole-2-sulfenamide.

* * * * *